(12) United States Patent
Sato et al.

(10) Patent No.: US 11,717,219 B2
(45) Date of Patent: Aug. 8, 2023

(54) BIOLOGICAL INFORMATION MEASURING APPARATUS AND BIOLOGICAL INFORMATION MEASURING SYSTEM

(71) Applicant: Agama-X Co., Ltd., Tokyo (JP)

(72) Inventors: Masahiro Sato, Tokyo (JP); Motofumi Baba, Tokyo (JP); Monta Ido, Tokyo (JP); Masayoshi Nakao, Tokyo (JP); Kengo Tokuchi, Tokyo (JP)

(73) Assignee: Agama-X Co., Ltd., Tokyo (JP)

( * ) Notice: Subject to any disclaimer, the term of this patent is extended or adjusted under 35 U.S.C. 154(b) by 1003 days.

(21) Appl. No.: 16/508,391

(22) Filed: Jul. 11, 2019

(65) Prior Publication Data

US 2020/0237307 A1  Jul. 30, 2020

(30) Foreign Application Priority Data

Jan. 24, 2019  (JP) .................. 2019-010674

(51) Int. Cl.
| | |
|---|---|
| *A61B 5/00* | (2006.01) |
| *A61B 5/25* | (2021.01) |
| *A61B 5/291* | (2021.01) |
| *A61B 5/296* | (2021.01) |
| *A61B 5/304* | (2021.01) |
| *A61B 5/369* | (2021.01) |

(52) U.S. Cl.
CPC .............. *A61B 5/6817* (2013.01); *A61B 5/25* (2021.01); *A61B 5/291* (2021.01); *A61B 5/296* (2021.01); *A61B 5/304* (2021.01); *A61B 5/369* (2021.01); *A61B 5/683* (2013.01); *A61B 2562/0209* (2013.01)

(58) Field of Classification Search
CPC ........ A61B 5/6815–6817; A61B 5/291; A61B 5/369; A61B 5/683
See application file for complete search history.

(56) References Cited

U.S. PATENT DOCUMENTS

| | | | |
|---|---|---|---|
| 2014/0288447 A1* | 9/2014 | Luna | A61B 5/6838 600/508 |
| 2019/0046794 A1* | 2/2019 | Goodall | A61N 1/36014 |
| 2019/0192077 A1* | 6/2019 | Kaiser | G06F 3/015 |
| 2019/0282119 A1* | 9/2019 | Andersen | A61B 5/30 |

FOREIGN PATENT DOCUMENTS

| | | |
|---|---|---|
| JP | 2007021106 A | 2/2007 |
| JP | 2011-217986 A | 11/2011 |
| WO | 2018103861 A1 | 6/2018 |

OTHER PUBLICATIONS

Japanese Notice of Reasons for Refusal (dated Jan. 10, 2023) for corresponding JP Application No. 2019163048, 7 pages.

* cited by examiner

*Primary Examiner* — Scott M. Getzow
(74) *Attorney, Agent, or Firm* — Hoffman Warnick LLC

(57) ABSTRACT

A biological information measuring apparatus includes a first electrode provided in contact with a user's external auditory canal and a second electrode provided in contact with the user's concha cavum.

20 Claims, 14 Drawing Sheets

FIG. 12

| ELECTRODE POSITION | DIAGRAM | | POTENTIAL STABILITY |
|---|---|---|---|
| BACK OF HELIX | | | LESS THAN 50% |
| CONCHA CYMBA | | | LESS THAN 50% |
| CONCHA CAVUM | | | SUBSTANTIALLY 100% |

# BIOLOGICAL INFORMATION MEASURING APPARATUS AND BIOLOGICAL INFORMATION MEASURING SYSTEM

CROSS-REFERENCE TO RELATED APPLICATIONS

This application is based on and claims priority under 35 USC 119 from Japanese Patent Application No. 2019-010674 filed Jan. 24, 2019.

BACKGROUND

(i) Technical Field

The present disclosure relates to a biological information measuring apparatus and a biological information measuring system.

(ii) Related Art

Techniques for measuring biological information such as brain waves using electrodes are known.

In Japanese Unexamined Patent Application Publication No. 2011-217986, a technique for measuring brain waves using canal earphones provided with conductive members is described.

SUMMARY

Aspects of non-limiting embodiments of the present disclosure relate to stable measurement of biological information regarding a user.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided a biological information measuring apparatus including a first electrode provided in contact with a user's external auditory canal and a second electrode provided in contact with the user's concha cavum.

BRIEF DESCRIPTION OF THE DRAWINGS

An exemplary embodiment of the present disclosure will be described in detail based on the following figures, wherein:

FIG. 12 is a diagram illustrating a relationship between a position of an electrode and the stability of potential;

DETAILED DESCRIPTION

Figure 1:
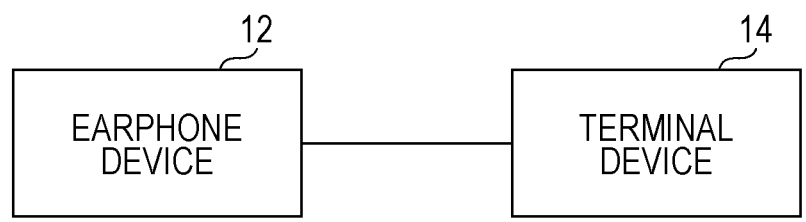
FIG. 1 is a block diagram illustrating a biological information measuring system according to an exemplary embodiment.

A biological information measuring system and a biological information measuring apparatus according to an exemplary embodiment of the present disclosure will be described hereinafter.

The biological information measuring apparatus according to the present exemplary embodiment is attached to user's ears and measures biological information regarding the user by measuring potential. The biological information is, for example, brain waves. It is needless to say that the biological information measuring apparatus may measure biological information other than brain waves (e.g., an electrocardiographic waveform or an electromyographic waveform). In the following description, the biological information measuring apparatus is used as a brain wave measuring apparatus, for example, and measures brain waves. The biological information measuring apparatus may be a so-called "bearable". The biological information measuring apparatus may be attached to one of the user's ears and measure the user's brain waves or attached to both of the user's ears and measure the user's brain waves. For example, a first biological information measuring apparatus may be attached to one of the user's ears, and a second biological information measuring apparatus may be attached to another of the user's ears. The first and second biological information measuring apparatuses may then measure the user's brain waves.

The biological information measuring apparatus includes one or a plurality of electrodes for detecting potential. In the present exemplary embodiment, a plurality of electrodes are attached to the user's ears, and at least two of the plurality of electrodes are used to measure the user's brain waves. When a biological information measuring apparatus includes a plurality of electrodes, for example, the biological information measuring apparatus is attached to one of the user's ears and at least two of the plurality of electrodes in contact with the ear are used to measure the user's brain waves. In another example, a biological information measuring apparatus including one or a plurality of electrodes may be attached to both of the user's ears, and at least two of the plurality of electrodes may be used to measure the user's brain waves. That is, at least two of a plurality of electrodes provided for one of the user's ears may be used to measure the user's brain waves, or at least two of a plurality of electrodes provided for both of the user's ears may be used to measure the user's brain waves. Alternatively, at least three of a plurality of electrodes may be used to measure the user's brain waves. The accuracy of measuring brain waves might improve by using more electrodes. In addition, electrodes used for measuring brain waves may be switched among a plurality of electrodes. For example, electrodes used to measure brain waves are switched in accordance with measurement conditions such as potential detection sensitivity and noise. One of a plurality of electrodes, for example, is used as an electrode for detecting brain waves (hereinafter referred to as a "sensor electrode"), and another electrode is used as an electrode for grounding (hereinafter referred to as a "ground electrode"). An electrode for detecting a reference signal to be compared with detected brain waves (hereinafter referred to as a "reference electrode") may also be used.

The biological information measuring apparatus may be incorporated into an object or a device attached to the ears such as earphones, hearing aids, earrings, a clip-like object, or glasses, or may be used along with such an object or a device. A case where the biological information measuring apparatus is incorporated into earphones will be described hereinafter as an example.

The biological information measuring system including the biological information measuring apparatus according to the present exemplary embodiment will be described hereinafter with reference to FIG. 1. FIG. 1 is a block diagram illustrating the configuration of a biological information measuring system 10 according to the present exemplary embodiment.

The biological information measuring system 10 as an example of an information processing system includes an earphone device 12 and a terminal device 14. The earphone device 12 and the terminal device 14 communicate with each other through a communication path. Wireless communication or wired communication is performed. The biological information measuring system 10 may include an apparatus such as a server.

The earphone device 12 is canal earphones, for example, and inserted into the external auditory canals of the ears. The earphone device 12 has, as earphones, a function of converting electrical signals output from a playback device into sound waves using speakers. The earphone device 12 includes the biological information measuring apparatus and measures the skin potential of the user's head. The earphone device 12 then outputs information indicating a result of the measurement (e.g., a signal indicating a measured potential or a brain wave signal generated by analyzing the measured potential) to an external device such as the terminal device 14 as information indicating a result of measurement of brain waves.

The earphone device 12 has, for example, a wireless communication function. A communication method such as short-distance wireless communication (e.g., Bluetooth (registered trademark) or radio-frequency identification (RFID)), infrared communication, visible light communication, or Wi-Fi (registered trademark) communication is used. The earphone device 12 receives sound signals such as audio signal from the terminal device 14 through wireless communication, for example, and generates sound in accordance with the sound signals. The earphone device 12 also transmits information indicating a result of measurement of brain waves to the terminal device 14 through wireless communication. Alternatively, the earphone device 12 may receive sound signals through wired communication and transmit information indicating a result of measurement of brain waves through wired communication.

The terminal device 14 is, for example, a personal computer (PC), a mobile terminal (e.g., a smartphone, a mobile phone, or a tablet PC), a music player, a movie playback device, or the like and corresponds to an example of an information processing device. The terminal device 14 has, for example, a wireless communication function. The terminal device 14 may function as a playback device to playback music and transmit sound signals to the earphone device 12 through wireless communication. The terminal device 14 may also have a function of receiving information indicating a result of measurement of brain waves from the earphone device 12 through wireless communication and evaluating a state of brain waves by analyzing the result of the measurement of brain waves. The earphone device 12 may analyze the result of the measurement of brain waves and transmit information indicating a result of the analysis to the terminal device 14 or another device. The terminal device 14 may transmit sound signals through wired communication and receive information indicating a result of measurement of brain waves through wired communication. The terminal device 14 may communicate with another device through a communication path such as a local area network (LAN) and communicate information through the Internet.

Figure 2:
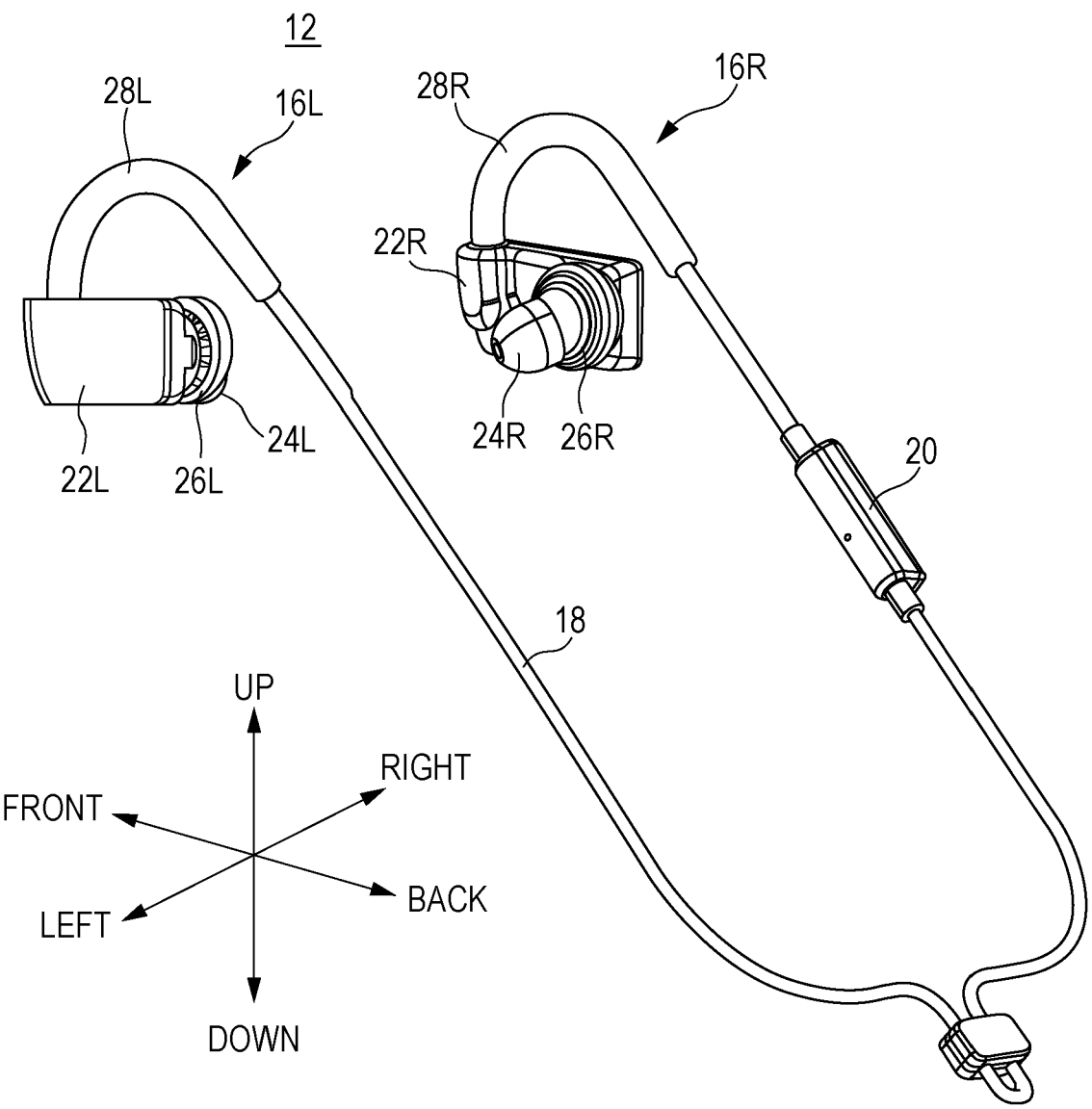
FIG. 2 is a perspective view of the entirety of an earphone device according to the exemplary embodiment.
Figure 3:
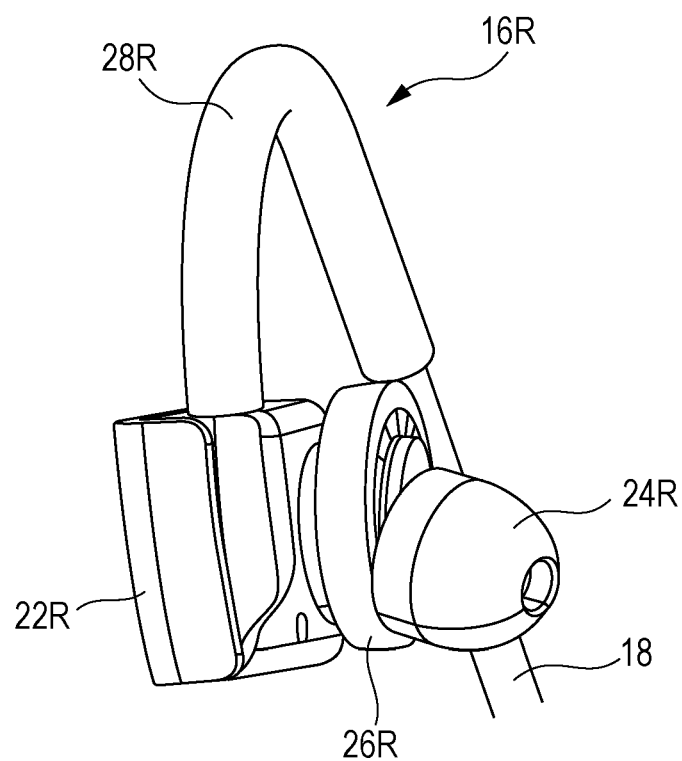
FIG. 3 is a perspective view of a right earphone unit.
Figure 4:
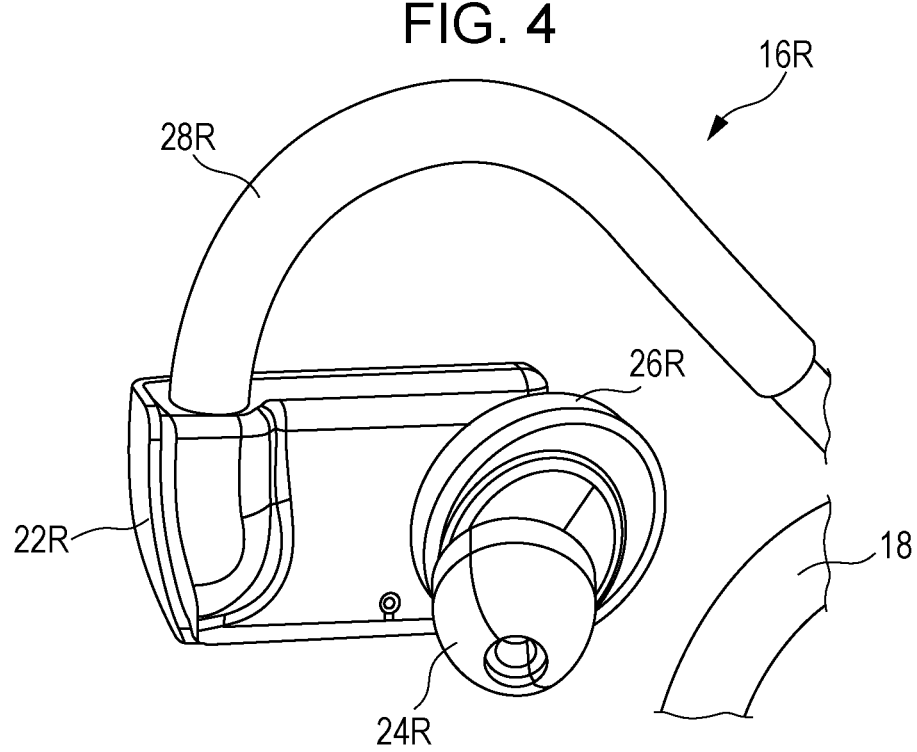
FIG. 4 is another perspective view of the right earphone unit.

A shape of the earphone device 12 according to the present exemplary embodiment will be described in detail hereinafter with reference to FIGS. 2 to 4. FIG. 2 is a perspective view of the entirety of the earphone device 12. FIGS. 3 and 4 are perspective views of a right earphone unit.

Directions of front, back, up, down, left, and right are defined as illustrated in FIG. 2 for the sake of convenience of description. The front direction is a direction in which the user's face is directed, and the back direction is a direction opposite the front direction. The up direction is a direction in which the top of the user's head is directed, and the down direction is a direction opposite the top direction. The left and right directions are directions of the user's left and right hands, respectively. A front-and-back direction, an up-and-down direction, and a left-and-right direction are perpendicular to one another.

As illustrated in FIG. 2, the earphone device 12 includes a right earphone unit 16R attached to the user's right ear, a left earphone unit 16L attached to the user's left ear, and a cable 18 that electrically connects the right earphone unit 16R and the left earphone unit 16L to each other. The cable 18 is provided with a remote control 20 for operating the earphone device 12. The remote control 20 need not necessarily be provided.

Either the right earphone unit 16R or the left earphone unit 16L may function as a biological information measuring apparatus that measures brain waves, or both the right earphone unit 16R and the left earphone unit 16L may function as biological information measuring apparatuses. Alternatively, either the right earphone unit 16R or the left earphone unit 16L may function as a biological information measuring apparatus, and the other may function as an apparatus that detects a reference signal or an apparatus used for grounding.

The right earphone unit 16R includes a right storage section 22R, a right earpiece 24R that functions as a first assistance unit, a right assistance section 26R that functions as a second assistance unit, and a right ear hook section 28R that functions as a restriction member. As the right earphone unit 16R, a known canal earphone may be used. A term "earpiece" or "ear pad" may be used, instead.

The right storage section 22R is, for example, a thin rectangular parallelepipedic case storing a board that functions as a processing device. The right earpiece 24R is provided on a surface of the right storage section 22R that faces the user's right ear when the user wears the earphone device 12. The right storage section 22R stores a control device, a speaker, a communication device (e.g., a communication chip), a brain wave measuring electronic circuit, a six-axis sensor (e.g., a sensor including a three-axis sensor that detects acceleration and a three-axis sensor that detects angular velocity), a memory, and the like. The communication device achieves a wireless communication function such as Bluetooth. The brain wave measuring electronic circuit generates brain waves by analyzing detected potential. The six-axis sensor detects movement direction, orientation, and rotation of the right storage section 22R. Information indicating a result of measurement of brain waves is stored in the memory. When the terminal device 14 is provided with a brain wave measuring unit, the brain wave measuring electronic circuit need not be provided for the earphone device 12.

The right earpiece 24R protrudes from the surface of the right storage section 22R. The right earpiece 24R stores a sound conduit and the like, and a sound output from the speaker goes out through the right earpiece 24R. An electrode for detecting potential is provided on an outer surface (e.g., a side surface) of the right earpiece 24R. The electrode may be, for example, a piece of conductive rubber composed of carbon.

The right assistance section 26R is provided between the right storage section 22R and the right earpiece 24R. The outer diameter of the right assistance section 26R is greater than that of the right earpiece 24R. An electrode for detecting potential is provided on an outer surface of the right assistance section 26R. The electrode may be, for example, a piece of conductive rubber composed of carbon.

The right earpiece 24R and the right assistance section 26R are elastic members. The elastic members may be composed of, for example, a resin such as rubber. More specifically, Si-based rubber (e.g., S1734 manufactured by NOK Corporation), urethane-based rubber, or the like may be used for the right earpiece 24R and the right assistance section 26R. A level of hardness (e.g., hardness according to a standard of durometer type A (instant)) of the right earpiece 24R and the right assistance section 26R is, for example, 40 to 75. In an example, a resin having a level of hardness of 70 may be used for the right earpiece 24R and the right assistance section 26R.

As described later, the right earpiece 24R is inserted into and comes into contact with the external auditory canal of the right ear. The right assistance section 26R comes into contact with the concha cavum of the right ear.

The right ear hook section 28R is a curved member hung on the helix of the user's right ear when the user wears the earphone device 12. One end of the right ear hook section 28R is connected to a front part of the right storage section 22R. The right ear hook section 28R is curved toward a back part of the right storage section 22R from a connection with the right storage section 22R, and this portion forms a curved portion. The curved portion is hung on the helix of the user's right ear. Another end of the right ear hook section 28R is connected to an end of the cable 18.

The right earpiece 24R and the right assistance section 26R are replaceable members. A plurality of types (e.g., three to five types) of right earpiece 24R and right assistance section 26R that vary in shape and size are prepared, for example, and the right earpiece 24R and the right assistance section 26R can be replaced in accordance with the shape of the user's ear (e.g., the external auditory canal, the concha cavum, or another part).

The left earphone unit 16L includes a left storage section 22L, a left earpiece 24L that functions as a first assistance unit, a left assistance section 26L that functions as a second assistance unit, and a left ear hook section 28L that functions as a restriction member. As the left earphone unit 16L, a known canal earphone may be used.

The left storage section 22L is, for example, a thin rectangular parallelepipedic case. The left earpiece 24L is provided on a surface of the left storage section 22L that faces the user's left ear when the user wears the earphone device 12. The left storage section 22L stores a speaker, a battery, and the like. The battery supplies power to the right earphone unit 16R and the left earphone unit 16L to drive the right earphone unit 16R and the left earphone unit 16L. For example, the battery supplies power to the speaker, the devices, the circuits, and the like stored in the right storage section 22R and the speaker stored in the left storage section 22L. The battery also supplies power to the remote control 20 to enable the operation of the remote control 20.

The left earpiece 24L protrudes from the surface of the left storage section 22L. The left earpiece 24L stores a sound conduit and the like, and a sound output from the speaker goes out through the left earpiece 24L. An electrode for detecting potential is provided on an outer surface (e.g., a side surface) of the left earpiece 24L. The electrode may be, for example, a piece of conductive rubber composed of carbon.

The left assistance section 26L is provided between the left storage section 22L and the left earpiece 24L. The outer diameter of the left assistance section 26L is greater than that of the left earpiece 24L.

The left earpiece 24L and the left assistance section 26L are elastic members. The elastic members may be composed of, for example, a resin such as rubber. More specifically, Si-based rubber (e.g., S1734 manufactured by NOK Corporation), urethane-based rubber, or the like may be used for the left earpiece 24L and the left assistance section 26L. A level of hardness (e.g., hardness according to a standard of durometer type A (instant)) of the left earpiece 24L and the left assistance section 26L is, for example, 40 to 75. In an example, a resin having a level of hardness of 70 may be used for the left earpiece 24L and the left assistance section 26L.

As described later, the left earpiece 24L is inserted into and comes into contact with the external auditory canal of the left ear. The left assistance section 26L comes into contact with the concha cavum of the left ear.

The left ear hook section 28L is a curved member hung on the helix of the user's left ear when the user wears the earphone device 12. One end of the left ear hook section 28L is connected to a front part of the left storage section 22L. The left ear hook section 28L is curved toward a back part of the left storage section 22L from a connection with the left storage section 22L, and this portion forms a curved portion. The curved portion is hung on the helix of the user's left ear. Another end of the left ear hook section 28L is connected to an end of the cable 18.

The left earpiece 24L and the left assistance section 26L are replaceable members. A plurality of types (e.g., three to five types) of left earpiece 24L and left assistance section 26L that vary in shape and size are prepared, for example, and the left earpiece 24L and the left assistance section 26L can be replaced in accordance with the shape of the user's ear (e.g., the external auditory canal, the concha cavum, or another part).

An electrode for detecting potential is not provided on an outer surface of the left assistance section 26L. This is just an example, and an electrode may be provided on the outer surface of the left assistance section 26L, instead. The electrode may be, for example, a piece of rubber composed of carbon.

The left storage section 22L may store a control device, a communication device (e.g., a communication chip), a brain wave measuring electronic circuit, a six-axis sensor, a memory, and the like. In this case, the right storage section 22R need not store a control device, a communication device, a brain wave measuring electronic circuit, a six-axis sensor, a memory, and the like. Alternatively, both the right storage section 22R and the left storage section 22L may store these components. Alternatively, the right storage section 22R may store a battery, and the left storage section 22L need not store a battery. In this case, the battery supplies power to the right earphone unit 16R and the left earphone unit 16L. Alternatively, both the right storage section 22R and the left storage section 22L may store a battery, and either or both of the batteries may supply power to the right earphone unit 16R and the left earphone unit 16L.

The remote control 20 is provided with, for example, a power button and a volume button. The power button is used to turn on and off the earphone device 12. In addition, the earphone device 12 and the terminal device 14 may be paired with each other by operating the power button. Pairing may be performed, for example, by pressing the power button for a certain period of time or longer (e.g., by keeping the power button pressed down). In addition, measurement of brain waves may be started or stopped by operating the power button. For example, measurement of brain waves is started by operating the power button in accordance with a predetermined operation procedure, and stopped by operating the power button in accordance with another operation procedure. Songs may be skipped, for example, by operating the volume button.

Figure 5:
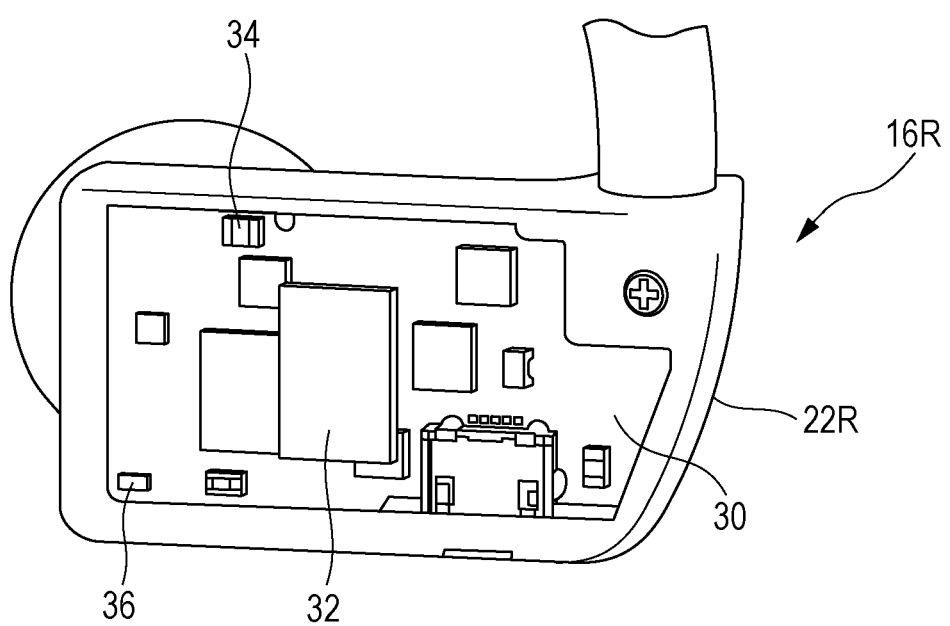
FIG. 5 is a perspective view of the inside of a right storage section.

Now, the components stored in the right storage section 22R will be described with reference to FIG. 5. FIG. 5 is a perspective view of the inside of the right storage section 22R.

The right storage section 22R stores a board 30, and the components such as the electronic circuits and the memory are mounted on the board 30. A communication chip 32, a brain wave measuring electronic circuit 34, a six-axis sensor 36, and the like, for example, are mounted on the board 30. Although not illustrated, chips for the memory and the control device are mounted on the board 30.

Figure 6:
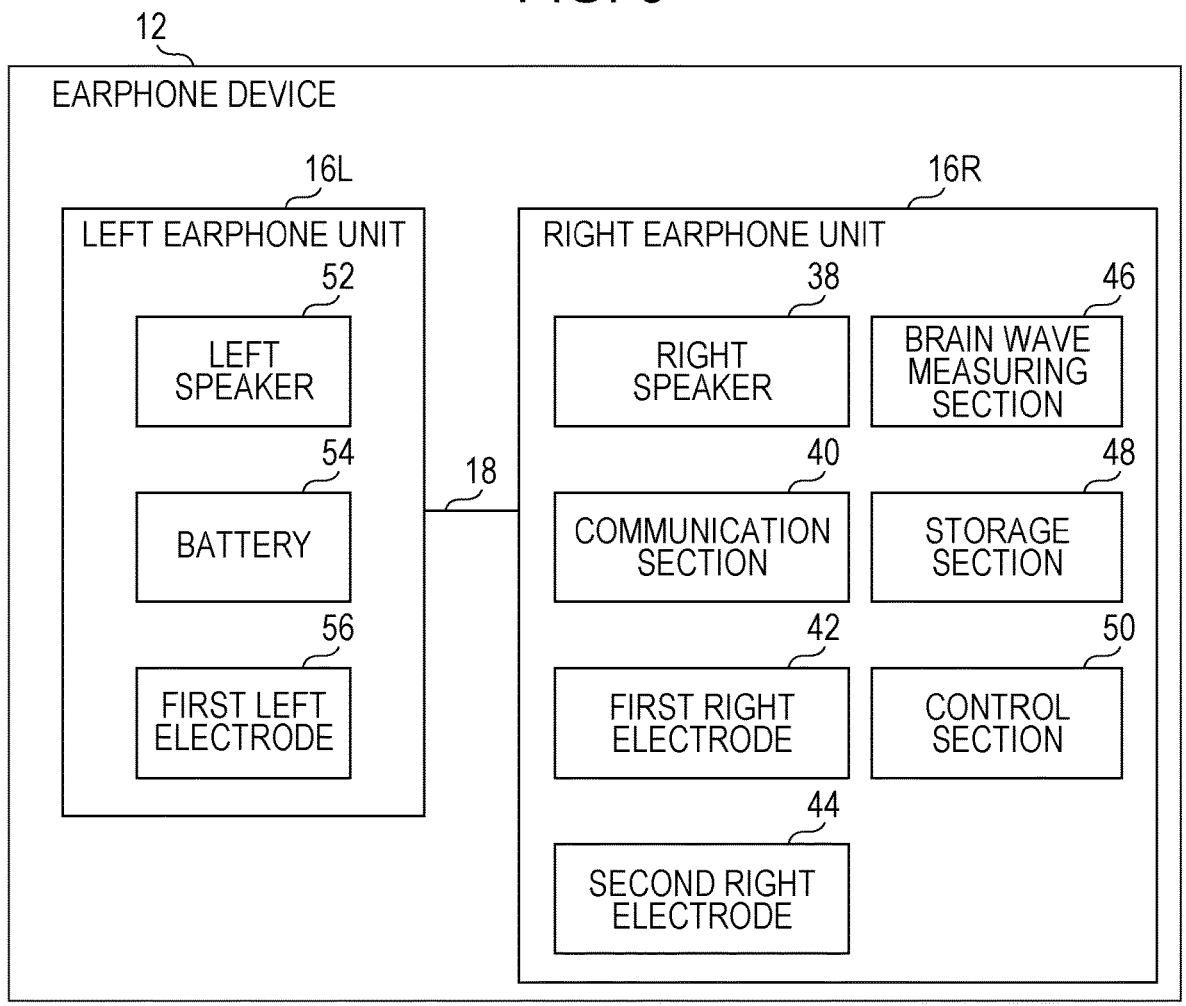
FIG. 6 is a block diagram illustrating the configuration of the earphone device.

Functions of the earphone device 12 will be described in detail hereinafter with reference to FIG. 6. FIG. 6 is a block diagram illustrating the functions of the earphone device 12.

As described above, the earphone device 12 includes the right earphone unit 16R, the left earphone unit 16L, and the cable 18. The right earphone unit 16R and the left earphone unit 16L are physical connected to each other by the cable 18 and communicate data with each other through the cable 18.

The right earphone unit 16R includes a right speaker 38, a communication section 40, a first right electrode 42, a second right electrode 44, a brain wave measuring section 46, a storage section 48, and a control section 50. The left earphone unit 16L includes a left speaker 52, a battery 54, and a first left electrode 56.

A sound output from the right speaker 38 goes out of the right earpiece 24R. A sound output from the left speaker 52 goes out of the left earpiece 24L.

The communication section 40 is a communication interface (e.g., a communication chip) and has a function of transmitting data to another apparatus and a function of receiving data from another apparatus. The communication section 40 is achieved by the communication chip 32. The communication section 40 has, for example, a wireless communication function. As the wireless communication function, short-distance wireless communication such as Bluetooth, infrared communication, visible light communication, and Wi-Fi communication, or the like is used as described above.

The communication section 40 receives, from the external device (e.g., the terminal device 14), signals indicating sounds to be output from the earphone device 12. For example, the communication section 40 receives, from the external device, a signal (hereinafter referred to as a "right sound signal") indicating a sound to be output from the right speaker 38 and a signal (hereinafter referred to as a "left sound signal") to be output from the left speaker 52. The right speaker 38 generates the sound in accordance with the right sound signal received by the communication section 40. The right earphone unit 16R transmits the left sound signal to the left earphone unit 16L through the cable 18. The left speaker 52 generates the sound in accordance with the left sound signal. Alternatively, the left earphone unit 16L may be provided with a communication section. In this case, the communication section may receive a left sound signal from the external device, and the left speaker 52 may generate a sound in accordance with the left sound signal.

The communication section 40 may transmit information indicating a result of measurement of brain waves to the external device (e.g., the terminal device 14). The communication section 40 corresponds to an example of an output unit.

The first right electrode 42 is the electrode provided on the outer surface of the right earpiece 24R. The second right electrode 44 is the electrode provided on the outer surface of the right assistance section 26R. Signals indicating potentials detected by the first right electrode 42 and the second right electrode 44 are output to the brain wave measuring section 46.

The first left electrode 56 is the electrode provided on the outer surface of the left earpiece 24L. The left earphone unit 16L outputs a signal indicating a potential detected by the first left electrode 56 to the brain wave measuring section 46 of the right earphone unit 16R through the cable 18.

The brain wave measuring section 46 calculates brain waves on the basis of potentials detected by the first right electrode 42, the second right electrode 44, and the first left electrode 56. The brain wave measuring section 46 is achieved by the brain wave measuring electronic circuit 34. The brain wave measuring section 46 corresponds to an example of a measurement unit.

The brain wave measuring section 46 may calculate brain waves on the basis of potentials detected by two electrodes selected from a group consisting of the first right electrode 42, the second right electrode 44, and the first left electrode 56.

For example, the first right electrode 42 is used as a sensor electrode for detecting brain waves, the second right electrode 44 is used as a ground electrode for grounding, and the first left electrode 56 is used as a reference electrode for detecting a reference signal to be compared with detected brain waves. For example, the brain wave measuring section 46 defines a potential detected by the second right electrode 44, which is the ground electrode, as a ground potential that serves as a reference potential. The brain wave measuring section 46 then calculates, as a result of measurement of brain waves, a difference between a potential of brain waves detected by the first right electrode 42, which is the sensor electrode, and the reference potential detected by the first left electrode 56, which is the reference electrode. Alternatively, the brain wave measuring section 46 may perform a known statistical process on the difference and employ a result of the statistical process as the result of the measurement of brain waves. Information indicating the result of the measurement of brain waves is temporarily stored in the storage section 48, for example, and the communication section 40 transmits the information to the terminal device 14 from the earphone device 12. Alternatively, the earphone device 12 may transmit signals indicating potentials before the calculation and a signal indicating a potential difference before the statistical process to the terminal device 14, and the terminal device 14 may calculate a potential difference and perform the statistical process. In this case, information indicating the potentials before the calculation and information indicating the potential difference before the statistical process correspond to the information indicating a result of measurement of brain waves.

The brain wave measuring section 46 may calculate a signal indicating brain waves by performing a calculation method (e.g., a known calculation method) other than one described above on potentials detected by the electrodes.

The storage section 48 is the memory, for example, and stores signals indicating potentials detected by the first right electrode 42, the second right electrode 44, and the first left electrode 56 and a signal indicating brain waves calculated by the brain wave measuring section 46.

The battery 54 supplies power to the components of the left earphone unit 16L and, through the cable 18, the components of the right earphone unit 16R. The components of the right earphone unit 16R and the left earphone unit 16L are driven by power supplied from the battery 54. A chargeable and dischargeable battery, for example, is used as the battery 54. Alternatively, a non-chargeable battery may be used. A shielding member for blocking electromagnetic waves may be provided around the battery 54 and other components relating to charging. When a shielding member is provided, noise due to electromagnetic waves caused during charging is reduced, and the accuracy of measuring brain waves improves.

The control section 50 controls the operation of the components of the right earphone unit 16R and the left earphone unit 16L. The control section 50 controls, for example, the communication performed by the communication section 40 and the operation of the battery 54. The control section 50 also performs operations in accordance with operations performed using the remote control 20. The control section 50 may also detect malfunctions of the components of the earphone device 12. The control section 50 is achieved, for example, by a microprocessor or the like.

The left earphone unit 16L, too, may be provided with a communication section 40, a brain wave measuring section 46, a storage section 48, a control section 50, and the like. The right earphone unit 16R, too, may be provided with a battery 54. Alternatively, these components may be provided for either the right earphone unit 16R or the left earphone unit 16L.

Although the right earphone unit 16R and the left earphone unit 16L are connected to each other by the cable 18, the earphone device 12 need not include the cable 18. In this case, a communication section is also provided inside the left earphone unit 16L, and the right earphone unit 16R and the left earphone unit 16L communicate data with each other.

Figure 7:
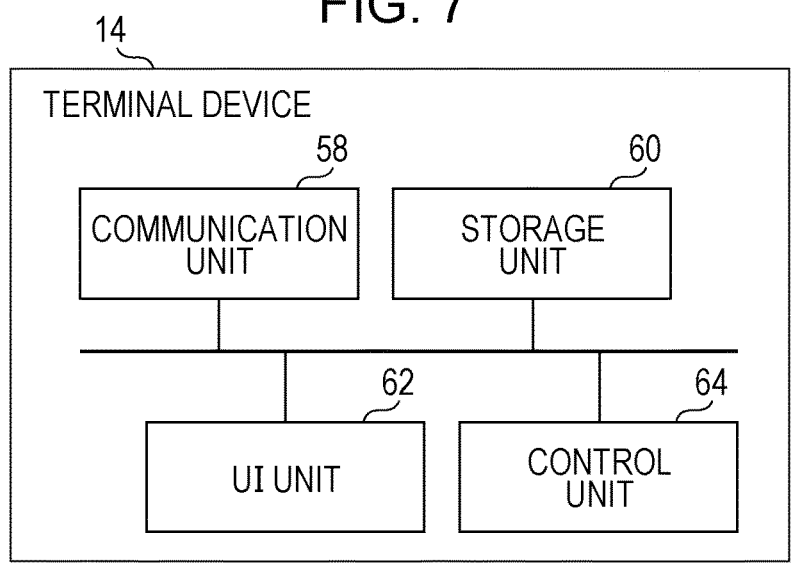
FIG. 7 is a block diagram illustrating the configuration of a terminal device.

Functions of the terminal device 14 will be described in detail hereinafter with reference to FIG. 7. FIG. 7 is a block diagram illustrating the functions of the terminal device 14.

A communication unit 58 is a communication interface and has a function of transmitting data to another apparatus and a function of receiving data from another apparatus. The communication unit 58 has, for example, a wireless communication function. Short-distance wireless communication such as Bluetooth, infrared communication, visible light communication, Wi-Fi communication, or the like is used for the function. Alternatively, the communication unit 58 may have a wired communication function.

The communication unit 58 communicates with the communication section 40 of the earphone device 12 through, for example, short-distance wireless communication. For example, the communication unit 58 transmits a sound signal to the earphone device 12 and receives a signal indicating a result of measurement of brain waves from the earphone device 12.

The communication unit 58 may communicate with another apparatus through a communication path such as the Internet using the wireless communication function such as Wi-Fi or the wired communication function.

The storage unit 60 is a storage device such as a hard disk drive or a memory. The storage unit 60 stores, for example, various pieces of data and various programs. For example, the storage unit 60 stores a signal indicating a result of measurement of brain waves performed by the earphone device 12.

The UI unit 62 is a user interface and includes, for example, a display section and an operation section. The display section is a display device such as a liquid crystal display or an electroluminescent (EL) display. The operation section is an input device such as a touch panel, buttons, a keyboard, or a mouse. The UI unit 62 may be a user interface that serves as both a display section and an operation section (e.g., a touch panel display or a device that displays an electronic keyboard on a display).

The control unit 64 controls the operation of the components of the terminal device 14.

The brain wave measuring section 46 may be provided for the terminal device 14, and the terminal device 14 may calculate a signal indicating brain waves by analyzing potentials detected by the electrodes of the earphone device 12. In this case, the brain wave measuring section 46 need not be provided for the earphone device 12.

Figure 8:
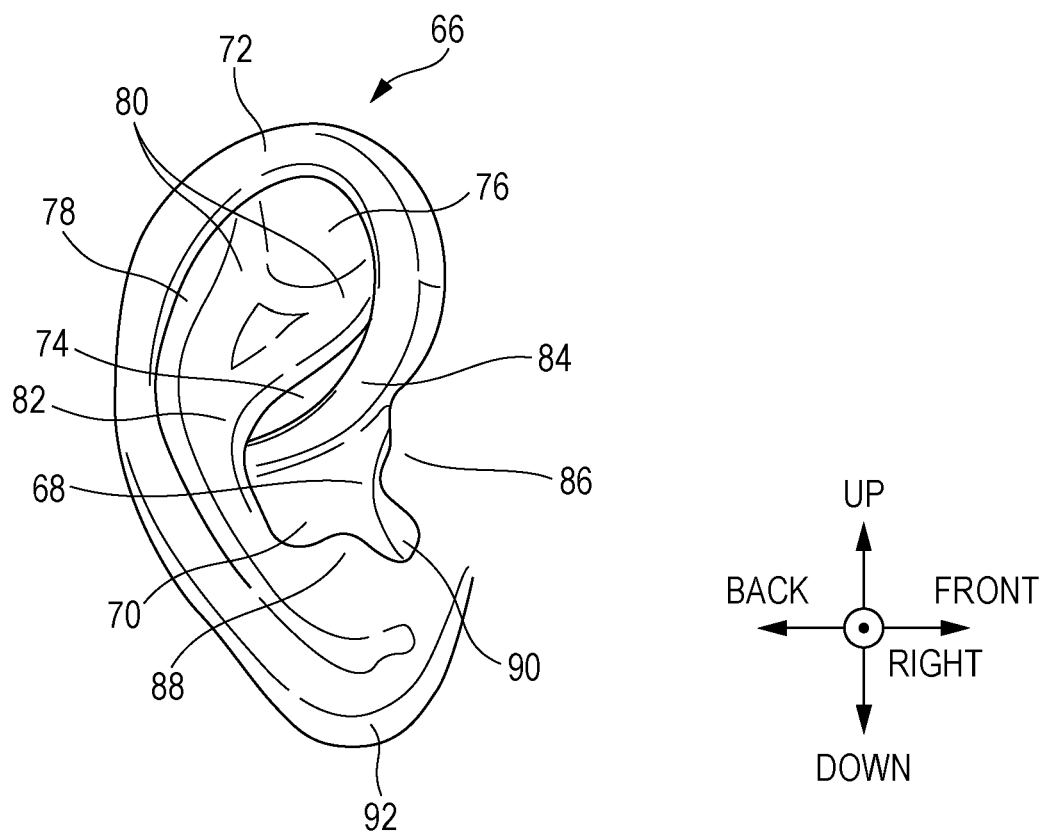
FIG. 8 is a diagram schematically illustrating the appearance of a human ear.
Figure 9:
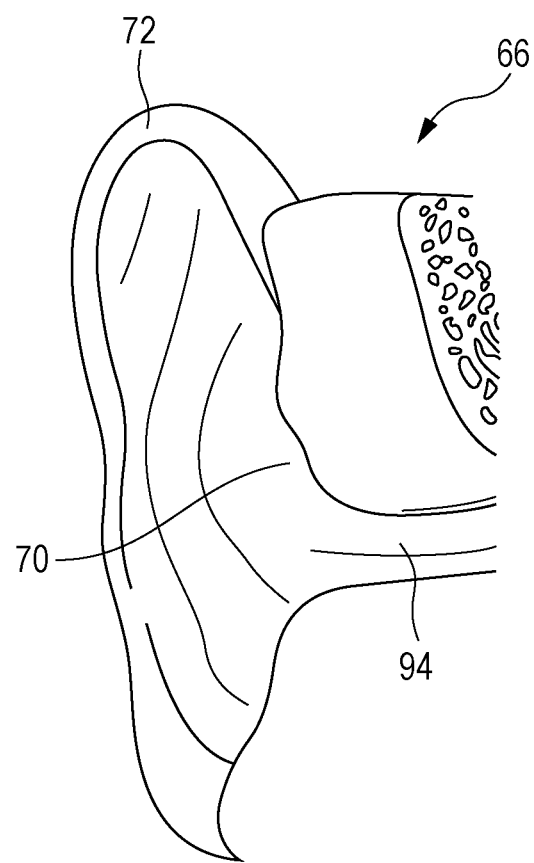
FIG. 9 is a diagram schematically illustrating the appearance and the inside of the human ear.
Figure 10:
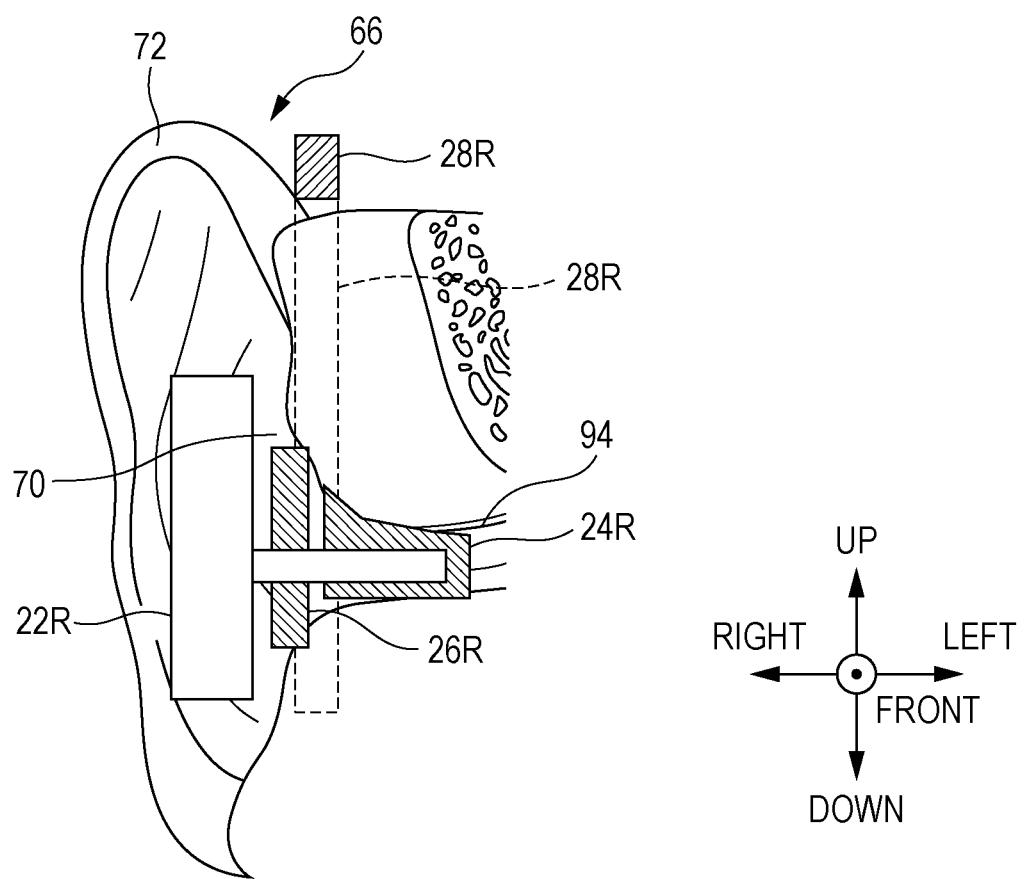
FIG. 10 is a diagram schematically illustrating the appearance and the inside of the human ear.
Figure 11:
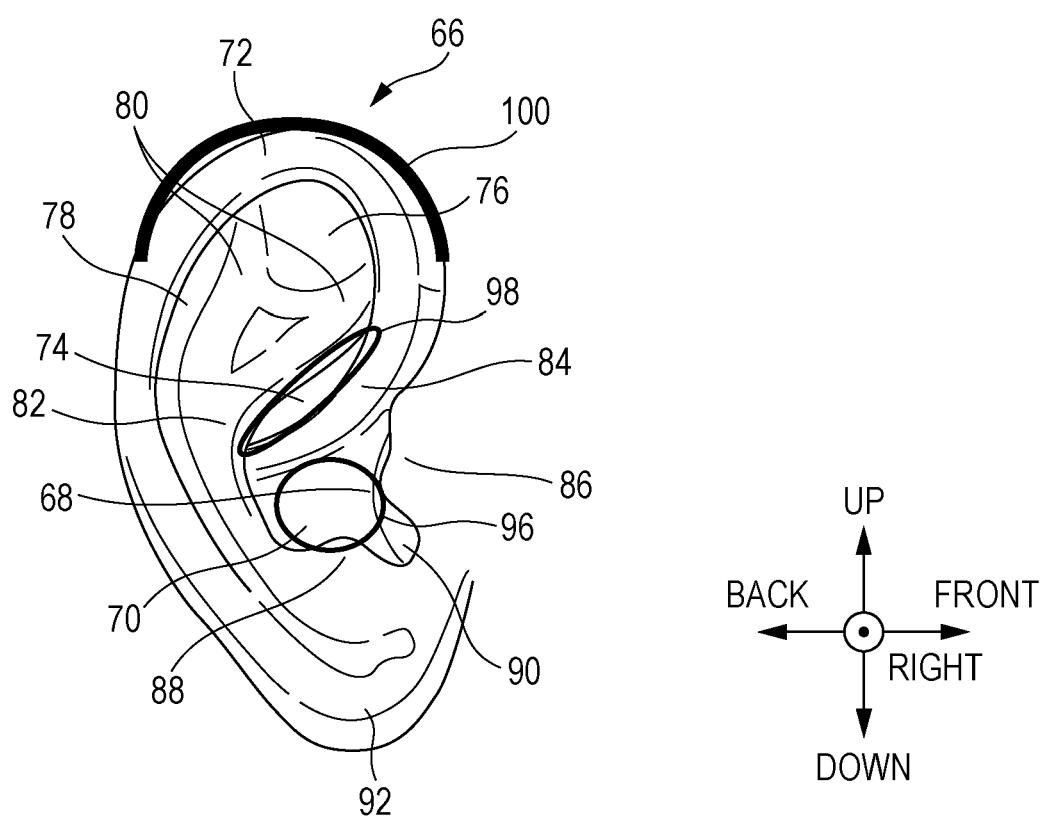
FIG. 11 is a diagram schematically illustrating the appearance of the human ear.

A state of contact between the earphone device 12 and the user's ear when the user wears the earphone device 12 will be described in detail hereinafter with reference to FIGS. 8 to 11. FIGS. 8 and 11 are diagrams schematically illustrating the appearance of a human ear. FIGS. 9 and 10 are diagrams schematically illustrating the appearance and the inside of the human ear. FIGS. 8 to 11 illustrate a right ear.

A human ear will be described with reference to FIGS. 8 and 9. An ear 66 includes an external auditory meatus 68 leading to an external auditory canal 94, a concha cavum 70, which is a part around the external auditory meatus 68, a helix 72, a concha cymba 74, a triangular fossa 76, a scaphoid fossa 78, crura antihelicis 80, an antihelix 82, a crus helicis 84, a tragus 86, an antitragus 88, an incisura 90, and a lobe 92.

FIG. 10 illustrates the right earphone unit 16R attached to the user's right ear (e.g., the ear 66). FIG. 11 illustrates parts 96, 98, and 100 in which the right earphone unit 16R is in contact with the user's right ear (e.g., the ear 66).

The right ear hook section 28R is hung on the helix 72, and the right earpiece 24R is inserted into the external auditory canal 94. At this time, the outer surface of the right earpiece 24R comes into contact with a surface (i.e., the skin) of the external auditory canal 94. Since the right earpiece 24R is an elastic member, the right earpiece 24R is deformed by the external auditory canal 94, and the outer surface of the right earpiece 24R is closely attached to the surface of the external auditory canal 94. As a result, the electrode (e.g., the first right electrode 42) on the outer surface of the right earpiece 24R is closely attached to the surface of the external auditory canal 94.

The right assistance section 26R comes into contact with the concha cavum 70. Since the right assistance section 26R is an elastic member, the right assistance section 26R is deformed by the concha cavum 70 and closely attached to the concha cavum 70. As a result, the electrode (e.g., the second right electrode 44) on the outer surface of the right assistance section 26R is closely attached to the concha cavum 70.

The movement of the right earphone unit 16R attached to the ear 66 is restricted because of the above-described configuration of the right earphone unit 16R. A mechanism of the restriction will be described in detail hereinafter.

The ear 66 (e.g., a root of the ear 66) is disposed between a lower part of the right ear hook section 28R and an upper part of the right assistance section 26R. That is, the ear 66 (e.g., the root of the ear 66) is sandwiched by the right ear hook section 28R and the right assistance section 26R in the up-and-down direction. As a result, the movement of the right earphone unit 16R is restricted in the up-and-down direction.

A right part of the right ear hook section 28R comes into contact with a part of the helix 72 of the user's right ear close to the head, and frictional force is caused between the outer surface of the right earpiece 24R and the external auditory canal 94. As a result, the movement of the right earphone unit 16R is restricted in the left-and-right direction.

In addition, the ear 66 (e.g., the root of the ear 66) is sandwiched by a part (e.g., a back part indicated by a broken line) of the right ear hook section 28R in contact with the back of the ear 66 and a back part of the right assistance section 26R in the front-and-back direction. As a result, the movement of the right earphone unit 16R is restricted in the front-and-back direction.

Since the movement of the right earphone unit 16R is restricted as described above, contact between the electrodes (e.g., the first right electrode 42 and the second right electrode 44) of the right earphone unit 16R and the skin is stably maintained. As a result, generation of noise that would otherwise mix into brain waves due to instable contact is prevented or suppressed, thereby improving the accuracy of measuring brain waves. Even if the user moves, for example, the movement of the right earphone unit 16R is restricted, and generation of noise is prevented or suppressed.

Depending on shapes of the user's ear and head, the ear 66 (e.g., the root of the ear 66) can be sandwiched by the lower part of the right ear hook section 28R and an upper part of the right earpiece 24R, and the movement of the right earphone unit 16R might be restricted in the up-and-down direction. In another case, the ear 66 (e.g., the root of the ear 66) can be sandwiched by a part (e.g., the back part indicated by the broken line) of the right ear hook section 28R in contact with the back of the ear 66 and a back part of the right earpiece 24R, and the movement of the right earphone unit 16R might be restricted in the front-and-back direction.

As described above, the right earpiece 24R, the right assistance section 26R, and the right ear hook section 28R function as assistance units or restriction units for positioning the right earphone unit 16R, that is, the electrodes to be in contact with the skin.

The same holds for the left earphone unit 16L. In the case of the left earphone unit 16L, the left earpiece 24L is inserted into the external auditory canal of the user's left ear, and the electrode (e.g., the first left electrode 56) on the left earpiece 24L comes into contact with a surface of the external auditory canal.

When the earphone device 12 according to the present exemplary embodiment is used, few hindrances are caused in real life compared to when a conventional brain wave measuring apparatus that measures brain waves by attaching a plurality of electrodes to a person's head (e.g., the scalp or the forehead is used). That is, because the conventional brain wave measuring apparatus that measures brain waves by attaching the plurality of electrodes to the scalp or the forehead does not assume use by a moving person, it is difficult and unrealistic for a person to move with the plurality of electrodes attached on his/her scalp or forehead. The earphone device 12 according to the present exemplary embodiment, on the other hand, is a bearable and the movement of the earphone device 12 is restricted. Even when a person wears the earphone device 12, the person can easily move around. Brain waves can therefore be accurately measured while the person is moving his/her body. For example, brain waves can be accurately measured while the person is working, walking, or running.

Although a shape of the ear varies between users, the right earpiece 24R, the right assistance section 26R, the left earpiece 24L, and the left assistance section 26L can be replaced by members of various sizes and shapes. Individual differences between users, therefore, do not pose a problem.

In addition, when the right storage section 22R stores the control device, the communication device, the brain wave measuring electronic circuit, and the like and the left storage section 22L stores the battery, weight is equally distributed between the two storage sections.

In the earphone device 12 according to the present exemplary embodiment, the control section 50 causes the electrode (e.g., the first right electrode 42) on the right earpiece 24R to function as a sensor electrode for detecting brain waves, the electrode (e.g., the second right electrode 44) on the right assistance section 26R to function as a ground electrode, and the electrode (e.g., the first left electrode 56) on the left earpiece 24L to function as a reference electrode for detecting a reference signal. The brain wave measuring section 46 measures brain waves on the basis of potential detected by these electrodes. The operations performed by the control section 50 may be performed by the control unit 64 of the terminal device 14, instead.

The control section 50 may change the functions (i.e., roles) of the electrodes. For example, the control section 50 may cause the first left electrode 56 to function as a sensor electrode, the first right electrode 42 as a reference electrode, and the second right electrode 44 as a ground electrode. Another combination may be employed, instead.

The control section 50 may change the functions of the electrodes on the basis of, for example, levels of magnitude or stability of potentials detected by the electrodes. For example, the control section 50 may cause an electrode that detects a highest potential or a most stable potential to function as a sensor electrode, an electrode that detects a second highest potential or a second most stable potential as a reference electrode, and the other electrode as a ground electrode.

Although three electrodes are used in the present exemplary embodiment, two electrodes may be used, instead. For example, the control section 50 causes the first right electrode 42 to function as a sensor electrode and the second right electrode 44 as a ground electrode, but disables the first left electrode 56. In this case, the brain wave measuring section 46 measures brain waves using potentials detected by the first right electrode 42 and the second right electrode 44 without using a potential detected by the first left electrode 56. Alternatively, the first right electrode 42 may be used as a ground electrode, and the second right electrode 44 may be used as a sensor electrode. In yet another example, the first left electrode 56 may be used as both a sensor electrode and a ground electrode.

Alternatively, four or more electrodes may be used. For example, a second left electrode may be provided for the left assistance section 26L. In this case, a plurality of electrodes are selected from the first right electrode 42, the second right electrode 44, the first left electrode 56, and the second left electrode, and the brain wave measuring section 46 measures brain waves on the basis of potentials detected by the plurality of electrodes. The control section 50 may select a plurality of electrodes on the basis of levels of magnitude or stability of potentials detected by the first right electrode 42, the second right electrode 44, the first left electrode 56, and the second left electrode.

Alternatively, three or more electrodes may be provided for either the right earphone unit 16R or the left earphone unit 16L, and the three or more electrodes may measure brain waves. In the right earphone unit 16R, for example, the first right electrode 42 may be provided for the right earpiece 24R, the second right electrode 44 may be provided for the right assistance section 26R, and a third right electrode may be provided for the right ear hook section 28R. In this case, the control section 50 causes the first right electrode 42, the second right electrode 44, and the third right electrode to function as a sensor electrode, a reference electrode, and a ground electrode, respectively. Three or more electrodes provided for an earphone unit may thus measure brain waves. The same holds for the left earphone unit 16L.

Although an electrode (e.g., the second right electrode 44 or the second left electrode) is provided for an assistance section (e.g., the right assistance section 26R or the left assistance section 26L) in such a way as to come into contact with the concha cavum 70 in the present exemplary embodiment, the electrode may be provided in such a way as to come into contact with a part other than the concha cavum 70, instead. For example, the electrode may be provided for an assistance section or a storage section in such a way as to come into contact with the concha cymba 74. Alternatively, the electrode may be provided for an ear hook section (e.g., the right ear hook section 28R or the left ear hook section 28L) in such a way as to come into contact with the helix 72. For example, the electrode may be provided for the right ear hook section 28R or the left ear hook section 28L, and the role of the electrode (e.g., the sensor electrode, the reference electrode, or the ground electrode) may be switched. The electrode may be provided in such a way as to come into contact with a part other than those described above. For example, the sensor electrode and the reference electrode may be provided in such a way as to increase a distance between the sensor electrode and the reference electrode.

Although the electrode may be provided at a part other than the concha cavum 70 as described above, potential measured by an electrode provided at the concha cavum 70 tends to be more stable than potential measured by an electrode provided at another part. A mechanism of this tendency will be described with reference to FIG. 12. FIG. 12 illustrates a result of evaluation of stability of potential measured by an electrode provided at different parts. In the example illustrated in FIG. 12, the electrode is provided at the back of the helix, the concha cymba, and the concha cavum and measures potential. In this example, the second right electrode 44 is provided. FIG. 12 includes photographs of the ear and schematic diagrams. The schematic diagrams of the ear are the same as that of FIG. 10 or the like. The second right electrode 44 is provided at positions indicated by arrows.

The number of subjects with whom electrical continuity has been observed is counted for each part, and the stability of potential is then evaluated on the basis of the number.

When the electrode is provided at the back of the helix, the number of subjects with whom electrical continuity has been observed is 10, which is lower than 50% of the total number of subjects. This might be because hair has gotten caught between the electrode and the helix or the electrode has come off from the skin.

When the electrode is provided at the concha cymba, a pin-shaped electrode is used. The number of subjects with whom electrical continuity has been observed is 10, which is lower than 50% of the total number of subjects. This might be because the electrode and the skin have been in contact with each other at a tip of the pin for more than half the subjects, and measured signals have been too weak. In addition, the shape of the concha cymba greatly varies between persons, and it is difficult to prepare an electrode suitable for each subject. If the ear is too small, for example, the pin might protrude from the ear. If the ear is too large, the pin might not be long enough. If a pin having a certain length is used, therefore, potential becomes stable or unstable depending on the subject. This might be why electrical continuity has been observed with only 10 subjects. The pin may be replaced with another pin, but various types of pin need to be prepared for the subjects, whose ears greatly vary in size.

When the electrode is provided at the concha cavum, electrical continuity has been observed with substantially all the subjects (substantially 100%), namely 35 subjects, by changing the size of the electrode in accordance with the size of the subjects' ears. Here, three electrodes that vary in size have been prepared, and one of the three electrodes has been selected for each subject in accordance with the size of the subject's ear.

Potential measured by an electrode provided at the concha cavum is thus more stable than potential measured by an electrode provided at the back of the helix or the concha cymba. This might be because of a contact area of the electrode, wearability, and other factors. Since potential can be measured even when an electrode is provided at the back of the helix or the concha cymba, however, an electrode may be provided at the back of the helix or the concha cymba.

In the present exemplary embodiment, elastic moduli of the elastic members of the right earpiece 24R and the right assistance section 26R may be the same or different from each other. For example, the elastic modulus of the right earpiece 24R may be higher than that of the right assistance section 26R. Alternatively, the elastic modulus of the right assistance section 26R may be higher than that of the right earpiece 24R. By adjusting the elastic moduli, the movement of the right earphone unit 16R caused by the movement of the user is absorbed by the right earpiece 24R and the right assistance section 26R. As a result, the right earphone unit 16R hardly, if at all, moves. The same holds for the left earphone unit 16L.

The earphone device 12 according to the present exemplary embodiment may be used along with a biological information measuring apparatus other than a brain wave measuring apparatus. Such a biological information measuring apparatus may be, for example, an electrocardiograph or an electromyograph. For example, potentials detected by a reference electrode and a ground electrode of the earphone device 12 may be used for an electrocardiograph or an electromyograph.

First Modification

Figure 13:
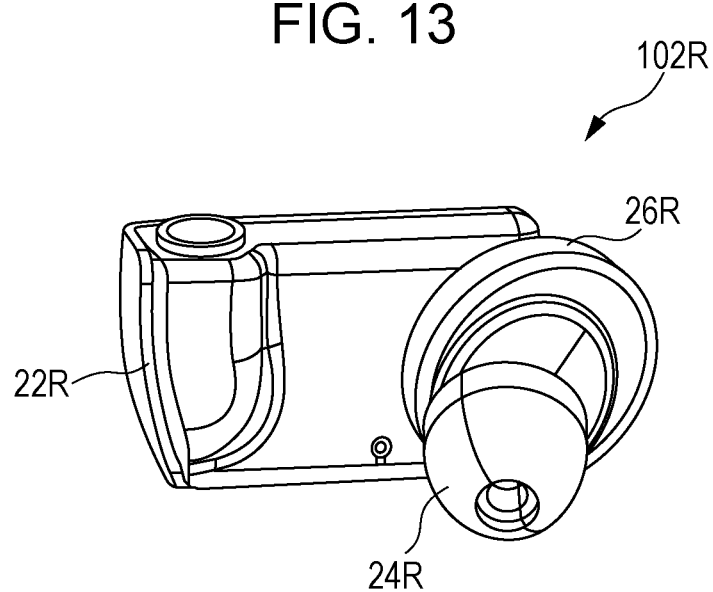
FIG. 13 is a perspective view of a right earphone unit according to a first modification of the exemplary embodiment.
Figure 14:
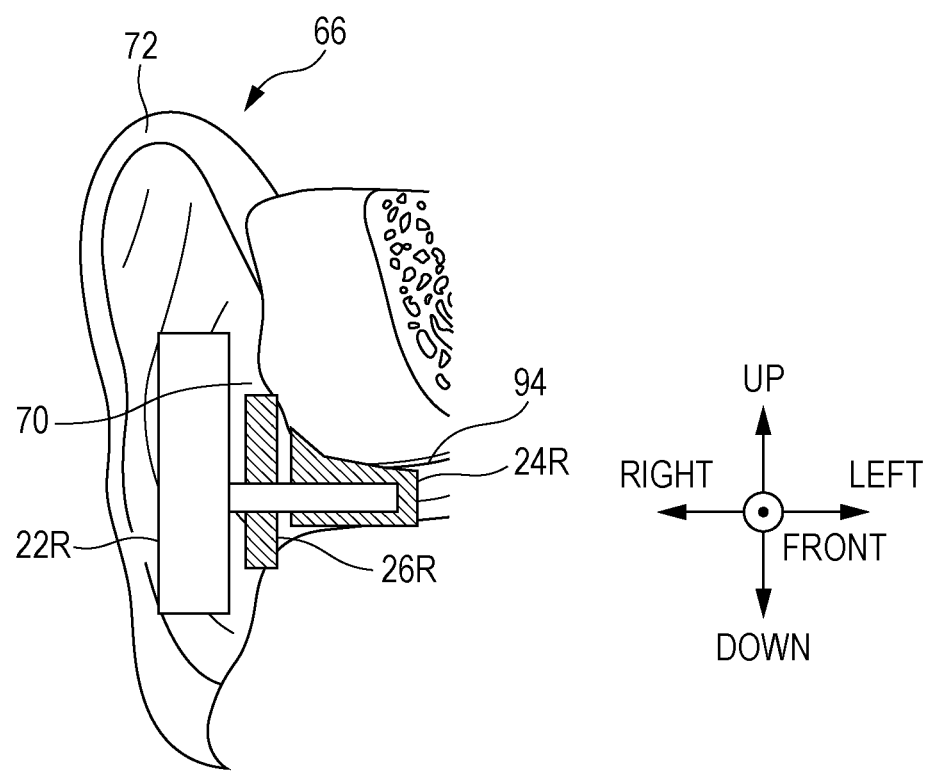
FIG. 14 is a diagram schematically illustrating the appearance and the inside of the human ear.

A first modification of the earphone device 12 according to the above exemplary embodiment will be described hereinafter with reference to FIGS. 13 and 14. FIG. 13 is a perspective view of a right earphone unit according to the first modification. FIG. 14 is a diagram schematically illustrating the appearance and the inside of the human ear. A right earphone unit 102R according to the first modification is different from the right earphone unit 16R in that the right earphone unit 102R does not include the right ear hook section 28R. Other components of the right earphone unit 102R are the same as those of the right earphone unit 16R. A left earphone unit, too, does not include the left ear hook section 28L as with the right earphone unit 102R, and other components of the left earphone unit are the same as those of the left earphone unit 16L.

FIG. 14 illustrates the right earphone unit 102R attached to the user's right ear (e.g., the ear 66). A state of contact between the right earpiece 24R or the right assistance section 26R and the skin is the same as when the right earphone unit 16R is used.

With the right earphone unit 102R according to the first modification, the movement of the right earphone unit 102R attached to the ear 66 is restricted. A mechanism of the restriction will be described in detail hereinafter.

The right earpiece 24R comes into contact with the surface of the external auditory canal 94, and the right assistance section 26R comes into contact with the concha cavum 70 in the up-and-down direction. As a result, the movement of the right earphone unit 102R is restricted in the up-and-down direction.

In addition, frictional force between the outer surface of the right earpiece 24R and the surface of the external auditory canal 94 restricts the movement of the right earphone unit 102R in the left-and-right direction.

In addition, the right earpiece 24R comes into contact with the surface of the external auditory canal 94, and the right assistance section 26R comes into contact with the concha cavum 70 in the front-and-back direction. As a result, the movement of the right earphone unit 102R is restricted in the front-and-back direction.

Since the movement of the right earphone unit 102R is restricted as described above, the contact between the electrodes (e.g., the first right electrode 42 and the second right electrode 44) of the right earphone unit 102R and the skin is maintained. As a result, generation of noise that would otherwise mix into brain waves due to instable contact is prevented or suppressed. The same holds for the left earphone unit according to the first modification.

Second Modification

Figure 15:
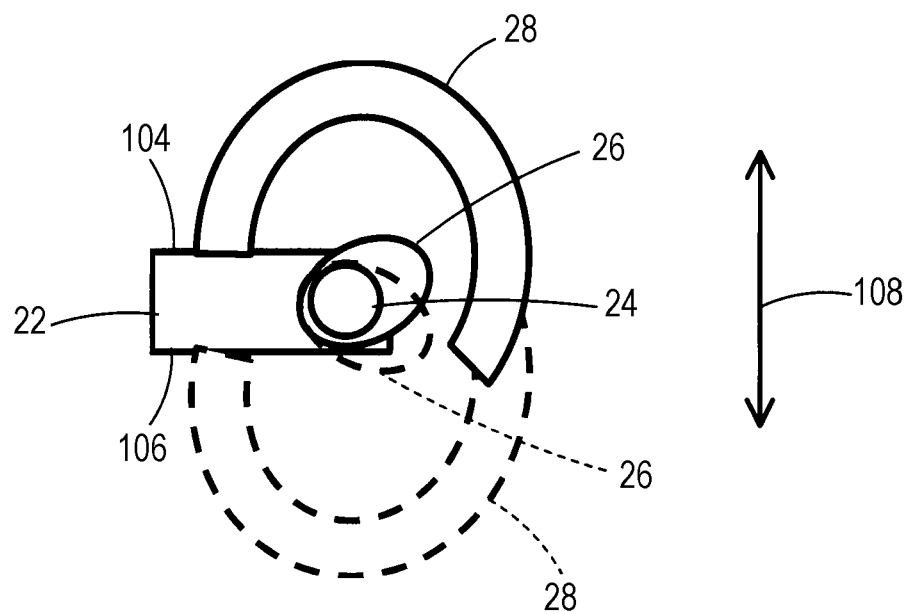
FIG. 15 is a diagram illustrating an earphone unit according to a second modification of the exemplary embodiment.

A second modification of the earphone device 12 according to the above exemplary embodiment will be described hereinafter with reference to FIG. 15. FIG. 15 is a diagram illustrating an earphone unit 16 according to the second modification viewed from a side of an earpiece.

In the second modification, an ear hook section as a restriction member is used as a mobile member. More specifically, the earphone unit 16 can be used as a right earphone unit or a left earphone unit by moving the ear hook section relative to a storage section. A mode for measuring biological information may be changed in accordance with the movement. The second modification will be described in detail hereinafter.

The earphone unit 16 illustrated in FIG. 15 includes, as with the right earphone unit 16R and the left earphone unit 16L, a storage section 22, an earpiece 24 that functions as a first assistance unit, an assistance section 26 that functions as a second assistance unit, and an ear hook section 28 that functions as a restriction member. Electrodes are provided on outer surfaces of the earpiece 24 and the assistance section 26. The electrodes may be provided for the ear hook section 28, instead, and roles of the electrodes may be switched.

The storage section 22 stores, for example, a control device, a speaker, a communication device (e.g., a communication chip), a brain wave measuring electronic circuit, a six-axis sensor, a memory, a battery, and the like.

The ear hook section 28 is removably attached to the storage section 22. Connection members (e.g., holes) for attaching the ear hook section 28 to the storage section 22, for example, are provided for an upper surface 104 (i.e., a surface directed upward when the user wears the earphone unit 16) and a lower surface 106 (i.e., a surface opposite the upper surface 104) of the storage section 22. The ear hook section 28 is attached to the storage section 22 by connecting an end of the ear hook section 28 to one of the connection members (e.g., by inserting the end into one of the connection members, namely holes). Wiring in the ear hook section 28 and a board in the storage section 22 are thus electrically connected to each other.

The assistance section 26 is provided for the storage section 22 in such a way as to be able to rotate in the up-and-down direction indicated by an arrow 108. For example, a part of the assistance section 26 (e.g., a part in which the earpiece 24 is provided) is attached to a side surface of the storage section 22 and serves as a rotational axis that allows the assistance section 26 to rotate in the up-and-down direction.

When the earphone unit 16 is used as a right earphone unit, the ear hook section 28 is attached to the upper surface 104 of the storage section 22 and the assistance section 26 is rotated upward (i.e., toward the upper surface 104) as indicated by solid lines in FIG. 15. The earphone unit 16 is attached to the user's right ear in this state. More specifically, the ear hook section 28 is hung on the helix of the user's right ear, the earpiece 24 is inserted into the external auditory canal of the user's right ear, and the assistance section 26 comes into contact with the concha cavum. As a result, the earphone unit 16 attached to the user's right ear measures potential.

When the earphone unit 16 is used as a left earphone unit, the ear hook section 28 is attached to the lower surface 106 of the storage section 22, and the assistance section 26 is rotated downward (i.e., toward the lower surface 106) as indicated by broken lines in FIG. 15. The earphone unit 16 is attached to the user's left ear in this state. More specifically, the ear hook section 28 is hung on the helix of the user's left ear, the earpiece 24 is inserted into the external auditory canal of the user's left ear, and the assistance section 26 comes into contact with the concha cavum of the user's left ear. As a result, the earphone unit 16 attached to the user's left ear measures potential.

The earphone unit 16 according to the second modification can thus be used as both a left earphone unit or a right earphone unit. That is, when the earphone unit 16 is used as a biological information measuring apparatus, the user's ear to which the earphone unit 16 is attached can be switched between the left ear and the right ear.

If the ear to which the earphone unit 16 is attached is switched, a control section (e.g., the control section 50) provided for the earphone unit 16 may enter a mode for measuring brain waves as biological information. This process will be described hereinafter.

Since the right ear is closer to the right brain and the left ear is closer to the left brain, sensitivity and a waveform of measured brain waves might differ between when the earphone unit 16 is attached to the right ear and when the earphone unit 16 is attached to the left ear. For this reason, a measurement mode is switched.

If the ear to which the earphone unit 16 is attached is switched (e.g., if the earphone unit 16 that has been attached to the right ear is attached to the left ear), for example, the control section 50 detects the switching using the six-axis sensor or the like. The control section 50 then compares sensitivity and a waveform of brain waves measured before the switching and sensitivity and a waveform of brain waves measured after the switching and measures brain waves in a measurement mode based on a result of the comparison. If the sensitivity decreases as a result of the switching, for example, the control section 50 enters a measurement mode with a higher level of sensitivity. It is assumed, for example, that the earphone unit 16 is switched from the right ear to the left ear. If the sensitivity of brain waves measured when the earphone unit 16 is attached to the left ear is lower than that of brain waves measured when the earphone unit 16 has been attached to the right ear, the control section 50 enters the measurement mode with a higher level of sensitivity. If the sensitivity increases as a result of the switching, the control section 50 may enter a measurement mode in which a level of sensitivity substantially equal to that before the switching is achieved or need not change the measurement mode.

Brain waves can thus be measured for each ear to which the earphone unit 16 is attached by changing the measurement mode after the ear to which the earphone unit 16 is attached is changed.

A mode for shaping a waveform of brain waves may be switched, or a mode for performing another type of signal processing may be switched, instead.

Third Modification

Figure 16:
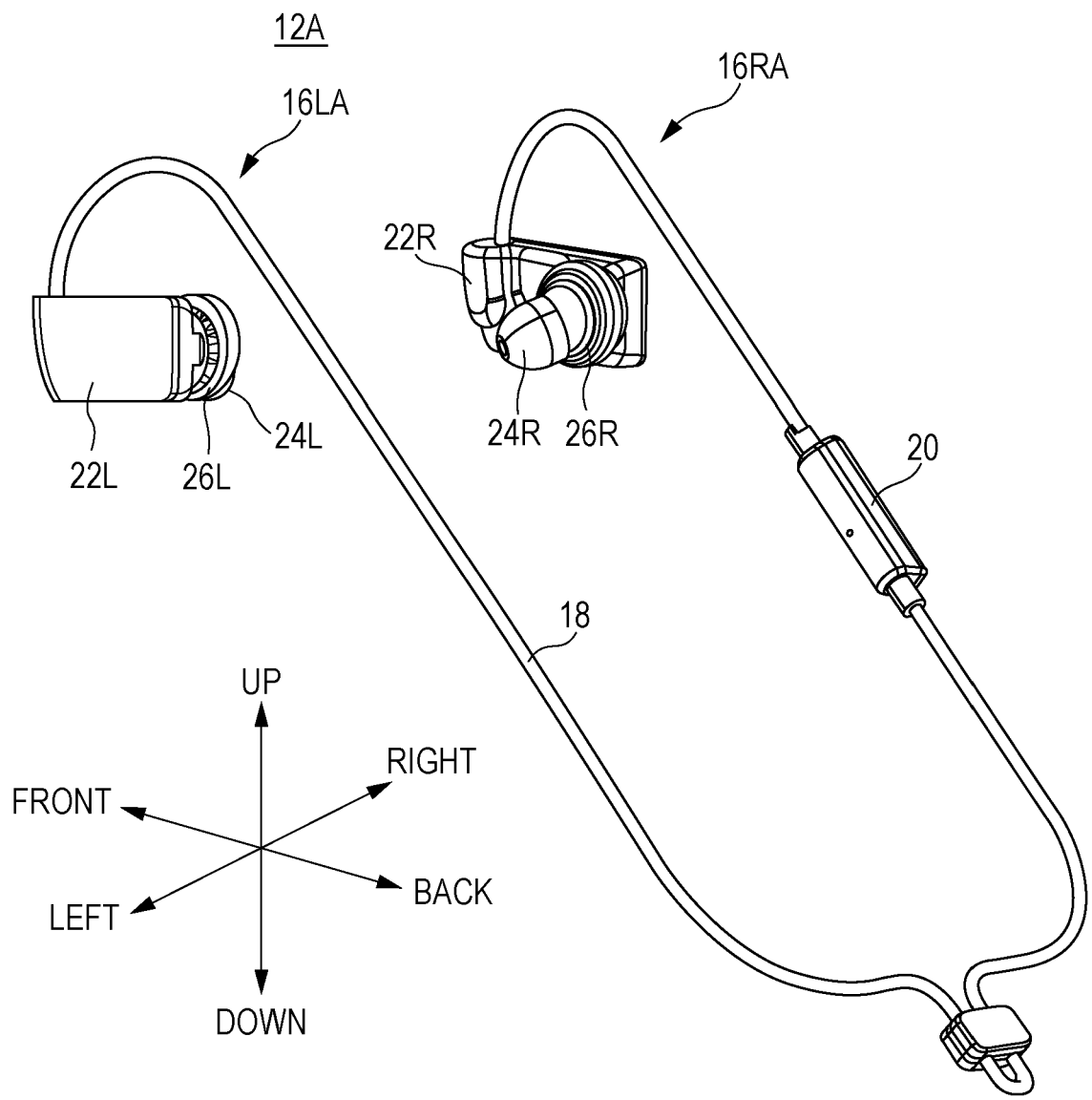
FIG. 16 is a perspective view of the entirety of an earphone device according to a third modification of the exemplary embodiment.
Figure 17:
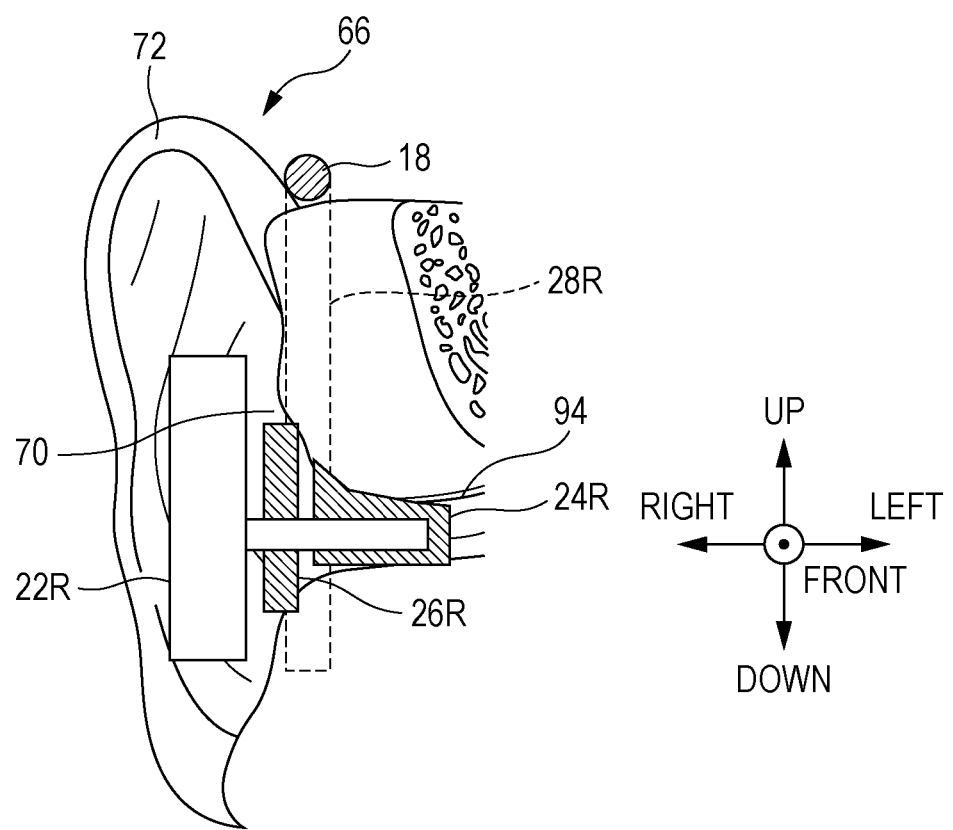
FIG. 17 is a diagram schematically illustrating the appearance and the inside of the human ear.

A third modification of the earphone unit 16 according to the above exemplary embodiment will be described hereinafter with reference to FIGS. 16 and 17. FIG. 16 is a perspective view of the entirety of an earphone device 12A according to the third modification. FIG. 17 is a diagram schematically illustrating the appearance and the inside of a human ear. FIG. 17 illustrates a right earphone unit attached to the right ear (e.g., the ear 66).

The earphone device 12A according to the third modification includes a right earphone unit 16RA and a left earphone unit 16LA instead of the right earphone unit 16R and the left earphone unit 16L. The earphone device 12A is not provided with the right ear hook section 28R or the left ear hook section 28L. As illustrated in FIG. 17, the cable 18 may be hung on the right ear (e.g., the helix 72) when the right earphone unit 16RA is attached to the right ear (e.g., the ear 66). Similarly, the cable 18 may be hung on the left ear when the left earphone unit 16LA is attached to the left ear.

In the third modification, as in the first modification, the movement of the right earphone unit 16RA and the left earphone unit 16LA is restricted, and contact between electrodes provided on the right earphone unit 16RA and the left earphone unit 16LA and the skin is maintained.

The foregoing description of the exemplary embodiment of the present disclosure has been provided for the purposes of illustration and description. It is not intended to be exhaustive or to limit the disclosure to the precise forms disclosed. Obviously, many modifications and variations will be apparent to practitioners skilled in the art. The embodiment was chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. A biological information measuring apparatus comprising:
    a first assistance unit including a first electrode, the first assistance unit configured to be inserted into a user's external auditory canal and the first electrode configured to be in contact with the user's external auditory canal; and
    a second assistance unit including a second electrode, the second electrode configured to be in contact with the user's concha cavum,
    wherein the second assistance unit and the first assistance unit are connected in sequence along a direction of insertion of the first assistance unit, and
    the second assistance unit is ring-shaped with a circumferential side configured to make contact with the user's concha cavum throughout.

2. The biological information measuring apparatus of claim 1,
    wherein the first and second assistance units restrict movement of the biological information measuring apparatus relative to the user.

3. The biological information measuring apparatus of claim 1,
    wherein the first and second assistance units are elastic members, and
    wherein the elastic moduli of the first and second assistance units are different from each other.

4. The biological information measuring apparatus of claim 3,
    wherein the elastic modulus of the first assistance unit is larger than the elastic modulus of the second assistance unit.

5. The biological information measuring apparatus of claim 3,
    wherein the elastic modulus of the second assistance unit is larger than the elastic modulus of the first assistance unit.

6. The biological information measuring apparatus of claim 1,
    wherein at least either the first assistance unit or the second assistance unit is replaceable.

7. The biological information measuring apparatus of claim 1, further comprising:
    a restriction member that restricts the movement of the biological information measuring apparatus relative to the user along with the first and second assistance units.

8. The biological information measuring apparatus of claim 7,
wherein the restriction member is a mobile member.

9. The biological information measuring apparatus of claim 1, further comprising:
an output unit that outputs signals measured by the first and second electrodes to an external device.

10. The biological information measuring apparatus of claim 1, further comprising:
a control unit that, if an ear to which the biological information measuring apparatus is attached is switched between the user's right ear and left ear, changes a mode for measuring biological information.

11. The biological information measuring apparatus of claim 1, further comprising a case, wherein the case, the second assistance unit and the first assistance unit are connected in sequence along the direction of insertion of the first assistance unit.

12. The biological information measuring apparatus of claim 11, wherein the case includes a processor.

13. The biological information measuring apparatus of claim 1, further comprising a case, wherein the case is located opposite the direction of insertion of the first assistance unit.

14. The biological information measuring apparatus of claim 13, wherein the case includes a processor.

15. The biological information measuring apparatus of claim 1, wherein the second electrode provided at the second assistance unit and the second assistance unit are configured to contact only the user's concha cavum.

16. The biological information measuring apparatus of claim 1, wherein the second assistance unit includes an axis of rotation along a direction of insertion of the first assistance unit into the user's external auditory canal.

17. A biological information measuring system comprising:
the biological information measuring apparatus of claim 1 attached to one of user's ears;
the biological information measuring apparatus of claim 1 attached to another of the user's ears; and
a measurement unit that measures biological information regarding the user electrodes included in the biological information measuring apparatuses attached to the user's ears.

18. The biological information measuring system of claim 17,
wherein the measurement unit measures the biological information regarding the user using a selected one of the electrodes.

19. The biological information measuring system of claim 17,
wherein the measurement unit measures the biological information regarding the user by causing one of the electrodes to function as an electrode for detecting the user's brain waves, another of the electrodes to function as an electrode for detecting a reference signal to be compared with the detected brain waves, and yet another of the electrodes to function as an electrode for grounding.

20. A biological information measuring system comprising:
the biological information measuring apparatus of claim 1 attached to one of user's ears;
an electrode attached to another of the user's ears; and
a measurement unit that measures biological information regarding the user using an electrode included in the biological information measuring apparatus attached to the one of the user's ears and the electrode attached to the other of the user's ears.

* * * * *